(12) United States Patent
Maples

(10) Patent No.: US 10,468,158 B2
(45) Date of Patent: Nov. 5, 2019

(54) APPARATUS AND METHOD FOR AN ELECTRO-MECHANICAL CABLE OVERSTRESS INDICATOR

(71) Applicant: SERCEL INC., Houston, TX (US)

(72) Inventor: Mike Maples, Houston, TX (US)

(73) Assignee: SERCEL, INC., Houston, TX (US)

( * ) Notice: Subject to any disclaimer, the term of this patent is extended or adjusted under 35 U.S.C. 154(b) by 762 days.

(21) Appl. No.: 14/271,852

(22) Filed: May 7, 2014

(65) Prior Publication Data

US 2015/0325336 A1    Nov. 12, 2015

(51) Int. Cl.
| | |
|---|---|
| *H01B 7/32* | (2006.01) |
| *H01B 7/14* | (2006.01) |
| *G01R 31/08* | (2006.01) |
| *G01N 19/08* | (2006.01) |
| *G01V 1/38* | (2006.01) |
| *G01V 1/20* | (2006.01) |

(52) U.S. Cl.
CPC .............. *H01B 7/326* (2013.01); *G01N 19/08* (2013.01); *G01R 31/08* (2013.01); *G01V 1/201* (2013.01); *G01V 1/3843* (2013.01); *H01B 7/14* (2013.01); *G01V 2001/204* (2013.01)

(58) Field of Classification Search
CPC .......... G01C 13/00; G01H 9/00; G01V 1/226; G01V 3/083; G02B 6/44; G02B 6/4401; G02B 6/4429; G02B 6/4433; H01B 7/00; H01B 7/10; H01B 7/32
USPC ........................................................ 324/539
See application file for complete search history.

(56) References Cited

U.S. PATENT DOCUMENTS

| | | | |
|---|---|---|---|
| 3,477,019 A | | 11/1969 | Hartmann |
| 3,610,808 A | * | 10/1971 | Horwinski ............... H01B 7/32 174/110 PM |
| 4,241,427 A | | 12/1980 | Swenson |
| 4,394,616 A | | 7/1983 | Browne et al. |
| 4,598,168 A | * | 7/1986 | Wagner .................... H01B 7/10 174/111 |
| 4,998,227 A | | 3/1991 | Rygg et al. |
| 5,303,202 A | | 4/1994 | Carroll et al. |
| 7,221,619 B1 | | 5/2007 | George |
| 2008/0053577 A1 | * | 3/2008 | Syed ....................... C22C 1/023 148/556 |
| 2008/0123467 A1 | | 5/2008 | Ronnekleiv et al. |
| 2011/0103180 A1 | | 5/2011 | Borgen |

(Continued)

FOREIGN PATENT DOCUMENTS

EP        2 814 041 A1    12/2014

OTHER PUBLICATIONS

Extended European Search Report in corresponding European Patent Application No. EP 14 17 7207 dated Oct. 27, 2015.

(Continued)

*Primary Examiner* — Akm Zakaria
(74) *Attorney, Agent, or Firm* — Patent Portfolio Builders PLLC

(57) ABSTRACT

An apparatus for indicating overstress in an electro-mechanical cable. The apparatus includes an overstress an overstress indicator cable including at least one non-twisted conductor disposed within a section of the electro-mechanical cable, where the non-twisted conductor is adapted to break when tension in the non-twisted conductor is greater than an allowable working load for the electro-mechanical cable.

20 Claims, 8 Drawing Sheets

(56) References Cited

U.S. PATENT DOCUMENTS

2012/0227504 A1* 9/2012 Goldner ............... G01H 9/00
                                                    73/655
2012/0315004 A1* 12/2012 Register, III ........ G02B 6/4433
                                                    385/101
2014/0253132 A1* 9/2014 Juhasz ................ G01V 3/083
                                                    324/365
2014/0368214 A1 12/2014 Despesse et al.

OTHER PUBLICATIONS

Office Action in European Application No. 14 177 207.9 dated Dec. 12, 2018. (All references not cited herewith have been previously made of record.).
Reed, D.A., et al.; "SEG Standards for marine seismic hydrophones and streamer cables"; Geophysics, XP055528975; vol. 52, No. 5; May 1, 1987 pp. 242-248.
Russian Official Action, dated Nov. 22, 2018, for related Russian Application No. 2015116431, along with a partial English Translation. (All references cited in the Russian Office Action are already of record.).
Chinese Office Action, dated Sep. 29, 2018, for related Chinese Application No. 201510226600.4, along with an English Translation. (All references cited in the Chinese Office Action are already of record.)

* cited by examiner

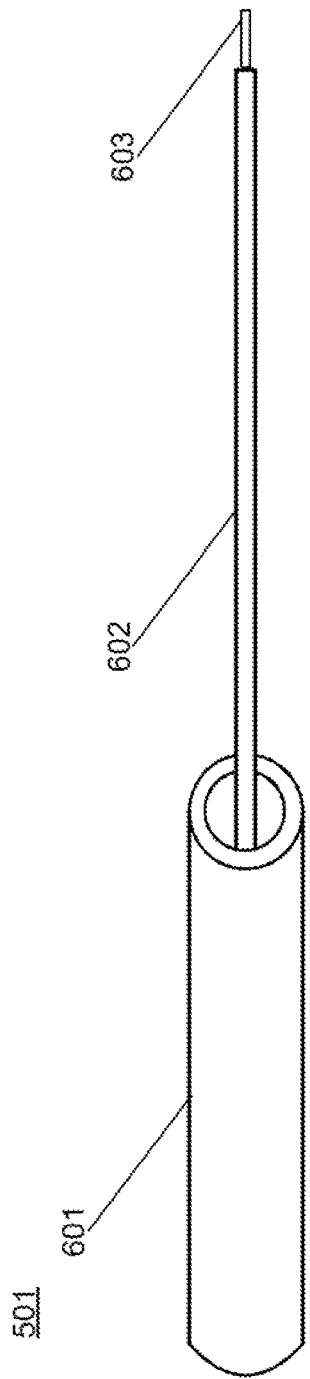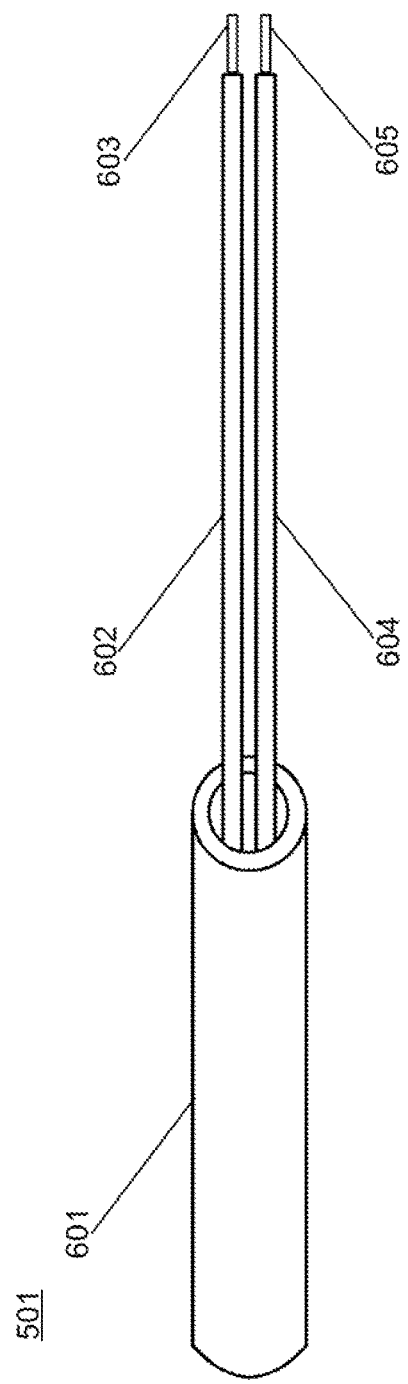

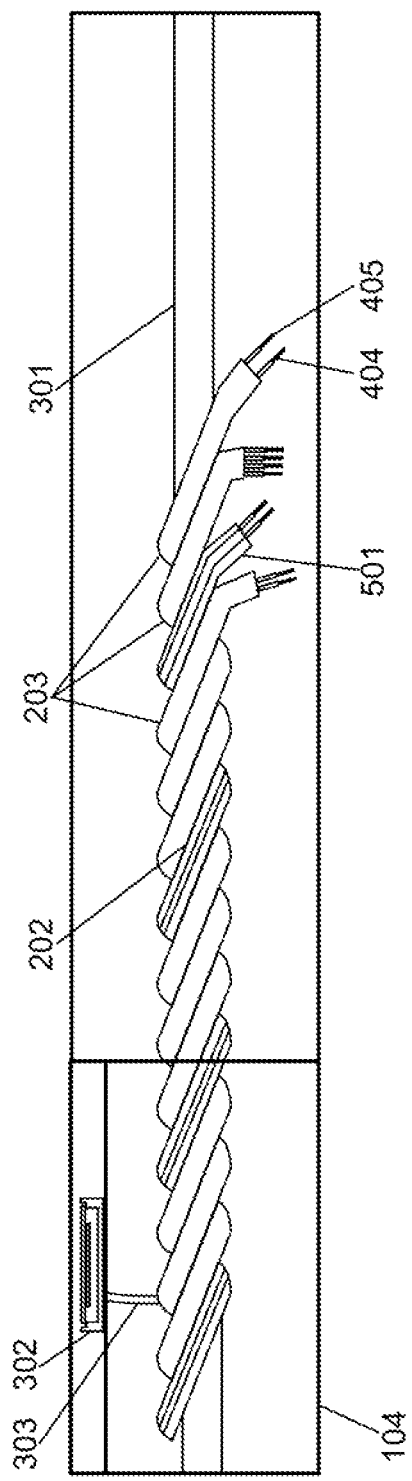

APPARATUS AND METHOD FOR AN ELECTRO-MECHANICAL CABLE OVERSTRESS INDICATOR

BACKGROUND

Technical Field

Embodiments of the subject matter disclosed herein generally relate to an apparatus and method for detecting and indicating overstress in an electro-mechanical cable.

Discussion of the Background

An electro-mechanical cable may be a cable, such as, for example, a marine-seismic cable, including sensor components, data-transmission cables, and strength enhancing and buoyancy enhancing components arranged in a single cable. A marine-seismic cable may be an electro-mechanical cable used for gathering data on the nature and composition of the earth below a body of water using seismic imaging techniques. FIG. 1 depicts an exemplary marine-seismic cable system in use. A marine vessel 101, including a cable reel 102, may deploy and tow an electro-mechanical cable 103, on or below the surface of the water. Seismic-imaging systems may make use of more than one. The electro-mechanical cable 103 may be up to 15 kilometers in length, and may be made up of shorter connected sections 201 of electro-mechanical cabling which may each be, for example, 110 meters to 200 meters in length. The sections 201 may be detachable from each other. The electro-mechanical cable 103 may be, for example, a marine-seismic cable or seismic streamer.

FIG. 2 depicts an exemplary section of an electro-mechanical cable including a view of a cabling layer. The section 201 of the electro-mechanical cable 103 may include various sensor components 104 inside of an outer jacket 105. The sensor components 104 may be, for example, hydrophones, geophones, accelerometers, electro-magnetic sensors, gravity sensors, or a combination thereof and may be distributed at regular intervals along the electro-mechanical cable 103. The outer jacket 105 may be, for example, a polyurethane jacket, and may be smooth in order minimize noise in the sensor components 104. A buoyant material may be contained in the electro-mechanical cable 103 inside the outer jacket 105, and may help keep the electro-mechanical cable 103 level on top of or under the water.

The section 201 of the electro-mechanical cable 103 may include a cabling layer 202. The cabling layer 202 may be a layer within the section 201 including various cables 203 wrapped in a helical manner around an inner strength member (not visible in FIG. 2). The cables 203 may be used, for example, for data and power transmission between the sensor components 104 and data processing equipment and power supplies located on the marine vessel 101 or deployed into the water from the marine vessel 101 separate from or as part of the electro-mechanical cable 103. The cables 203 may run the length of the section 201 and may connect to corresponding cables 203 in neighboring sections 201 of the electro-mechanical cable 103.

FIG. 3 depicts an exemplary portion of a section of an electro-mechanical cable including a view of internal cabling, cable conductors, and strength member. The cables 203 may include various types of cabling. For example, as depicted in FIG. 3, the cables 203 may include conductors in twisted pairs, twisted triples, and twisted quads. Note that the ends of the conductors within the cables 203 are depicted in FIG. 3 for illustrative purposes, and may not be visible in an assembled electro-mechanical cable 103. The cables 203 may be made of any suitable electrical conductor for data or power transmission, such as, for example, copper, in any suitable gauge, may be solid or stranded, and may be insulated and arranged in any suitable manner. The cables 203 may also include fiber optic cabling. FIG. 4 depicts an exemplary twisted pair cable. The cable 203 may include an outer insulation jacket 401, a first conductor 404 wrapped in a first inner insulation jacket 403, and a second conductor 405 wrapped in a second inner insulation jacket 402. The first inner insulation jacket 403 and second inner insulation jacket 402 may be twisted around each other, forming a twisted pair cable.

Returning to FIG. 3, the strength member 301 around which the cables 203 may be wrapped in the cabling layer 202 may be made of any suitable material in any suitable structure, such as, for example, a composite material or braided or helical steel rope. The strength member 301 may be flexible, to allow for and support the flexing of the electro-mechanical cable 103 that occurs in ordinary use. Alternatively, the strength member 301 may be wrapped helically or braided over the cables 203, which may be twisted together in helix, so that the cabling layer 202 is inside of the strength member 301. A piezoelectric pressure sensor or another sensor 302 in the sensor component 104 may be connected to one of the cables 203 by sensor cable 303, using any suitable interface, to relay collected sensor data back to the marine vessel 101 through cables 203.

The electro-mechanical cable 103, and each section 201 thereof, may be subject to various stresses during deployment, use, and retrieval. The electro-mechanical cable 103 may experience increases in tension while being unreeled, towed, and reeled back in. When part of the electro-mechanical cable 103 experiences tensions that exceed the allowable safe working load for the electro-mechanical cable 103, electrical conductors or fiber optics within the cables 203 of the section 201 subject to the excess tension, or overstress, may break. Breaks in any of the conductors in the cables 203 may impair the functioning of the electro-mechanical cable 103, necessitating stopping the entire survey and performing costly repairs. It may be useful to be able to determine whether a cable break was the result of an overstress condition in the electro-mechanical cable 103 or was a manufacturing defect.

Load cells or strain gauges may be used within the electro-mechanical cable 103 to detect excess tension and overstress conditions. However, both load cells and strain gauges may be expensive and may require electrical power and data transmission and storage capabilities for handling tension data that necessitate additional cabling within the electro-mechanical cable 103 and processing power and data storage onboard the marine vessel 101. This may either take away space, power, and data bandwidth from the sensor components 104, or result in the electro-mechanical cable 103 having added weight, complexity, and expense, due to the additional components and cabling that may be needed to operate load cells or strain gauges within the electro-mechanical cable 103. Excessive tension may also be created along the length of section 201 by localized cable bending in excess of the rated bend diameter. This localized bending will cause the outer electrical conductors or fiber optics within the cables 203 of the section 201 to experience overstress conditions and the conductors on inner portion of the bend will be forced into compression which can also damage the component. The high stresses created by localized bending would not be detected by load cell or strain gages.

Thus, there is a need for an apparatus and method for indicating overstress in an electro-mechanical cable without adding complexity to the cable.

SUMMARY

In various embodiments, an apparatus and method are provided for indicating overstress in an electro-mechanical cable.

In one embodiment, there is an apparatus for indicating overstress in an electro-mechanical cable. The apparatus includes an overstress indicator cable including at least one non-twisted conductor disposed within a section of the electro-mechanical cable, where the non-twisted conductor is adapted to break when tension in the non-twisted conductor is greater than an allowable working load for the electro-mechanical cable.

According to another embodiment, there is a method for detecting an overstress condition in an electro-mechanical cable. The method includes applying a voltage to a non-twisted conductor in an overstress indicator cable; measuring at least one of characteristic of a circuit formed by the non-twisted conductor and one of a second non-twisted conductor, a strength member, and a twisted conductor; comparing the measured characteristic to an expected value for the characteristic; and if the measured characteristic varies from the expected value for the characteristic by more than a predetermined amount, indicating that an overstress condition has occurred in the electro-mechanical cable.

According to yet another embodiment, there is an apparatus for indicating overstress in an electro-mechanical cable. The apparatus includes an outer jacket surrounding the electro-mechanical cable; a strength member disposed lengthwise within the electro-mechanical cable; foam disposed within the electro-mechanical cable; a seismic sensor component disposed within a sensor carrier disposed within the electro-mechanical cable; an overstress indicator cable, including at least two non-twisted conductors and an outer jacket, wrapped helically around the strength member within a cabling layer in the electro-mechanical cable, each non-twisted conductor including copper wire disposed within an outer insulation jacket, wherein the non-twisted conductors are adapted to break when tension in the non-twisted conductors is greater than an allowable working load of the electro-mechanical cable; a first connector and a second connector disposed within the electro-mechanical cable, wherein one end of the non-twisted conductors are connected to the first connector and the other end of the non-twisted conductors are connected to the second connector; and a monitoring device including at least one of an ammeter and an ohmmeter connected to the overstress indicator cable, wherein the monitoring device is adapted to apply a voltage to the non-twisted conductors and determine if one of the non-twisted conductors has broken based on based on measurements from the ammeter or ohmmeter and indicate that an overstress condition has occurred in the electro-mechanical cable when a non-twisted conductor is determined to be broken.

BRIEF DESCRIPTION OF THE DRAWINGS

The accompanying drawings, which are incorporated in and constitute a part of the specification, illustrate one or more embodiments and, together with the description, explain these embodiments. In the drawings:

FIGS. 6a and 6b depict exemplary non-twisted cables which may be used as an overstress indicator cable with one conductor and two conductors;

FIG. 7 depicts an exemplary portion of a section of an electro-mechanical cable including a view of the cabling layer with an overstress indicator cable, cable conductors, and strength member.

DETAILED DESCRIPTION

The following description of the exemplary embodiments refers to the accompanying drawings. The same reference numbers in different drawings identify the same or similar elements. The following detailed description does not limit the invention. Instead, the scope of the invention is defined by the appended claims. In various embodiments as illustrated in FIGS. 1-11, an overstress indicator apparatus is included in an electro-mechanical cable.

Reference throughout the specification to "one embodiment" or "an embodiment" means that a particular feature, structure or characteristic described in connection with an embodiment is included in at least one embodiment of the subject matter disclosed. Thus, the appearance of the phrases "in one embodiment" or "in an embodiment" in various places throughout the specification is not necessarily referring to the same embodiment. Further, the particular features, structures or characteristics may be combined in any suitable manner in one or more embodiments.

Figure 5:
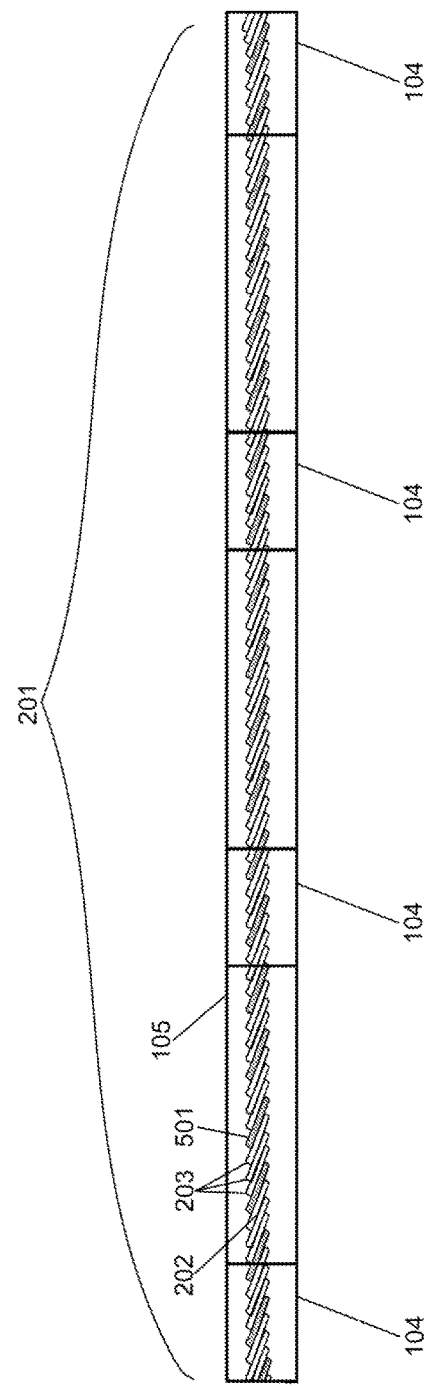
FIG. 5 depicts an exemplary section of an electro-mechanical cable including a view of a cabling layer with an overstress indicator cable.

FIG. 5 depicts an exemplary section of an electro-mechanical cable including a view of a cabling layer with an overstress indicator cable. An overstress indicator cable 501 may be included among the cables 203 in the cabling layer 202 wrapped helically around the strength member 301. The overstress indicator cable 501 may be a single continuous cable in the cabling layer 202 running the length of one of the sections 201 of the electro-mechanical cable 103. As depicted in FIG. 5, if, for example, the cabling layer includes three cables 203, every fourth winding around the strength member 301 may be the overstress indicator cable 501. The overstress indicator cable 501 may be wrapped around strength member 301 with a tighter gap than the cables 203 so that the indicator cable 501 is stressed more than the cables 203 when the section 201 is subject to overstress.

FIGS. 6a and 6b depict exemplary non-twisted cables which may be used as an overstress indicator cable with one conductor and two conductors. The overstress indicator cable 501 may be a single non-twisted cable, and may include, as depicted in FIG. 6a, an outer insulation jacket 601 and a first non-twisted conductor 603 wrapped in a first inner insulation jacket 602. Alternatively, the first non-twisted conductor may not be wrapped in the first inner insulation jacket 602, and may only be insulated by the outer insulation jacket 601. As depicted in FIG. 6b, the overstress indicator cable may also include a second non-twisted conductor 605 wrapped in a second inner insulation jacket 604. The non-twisted conductors 603 and 605 may be, for example, copper conductors. The overstress indicator cable 501, including either the non-twisted conductors 603 and 605 or just the non-twisted conductor 603, may be included in the cabling layer 202 where the other cables 203 may include conductors that are twisted pairs, twisted triples, twisted quads, or fiber optic cables. The non-twisted conductors 603 and 605 may be separate lengths of conductive materials, and may be connected into a circuit by a suitable connector such as, for example, a wiring harness, at either end of the electro-mechanical cable 103. Alternatively, if the overstress indicator cable 501 includes only one non-twisted conductor 603, a circuit may be completed using the non-twisted conductor 603 and the strength member 301, one of the cables 203, or any other suitable cable or length of conductive material within the section 201 of the electro-mechanical cable 103.

Figure 1:
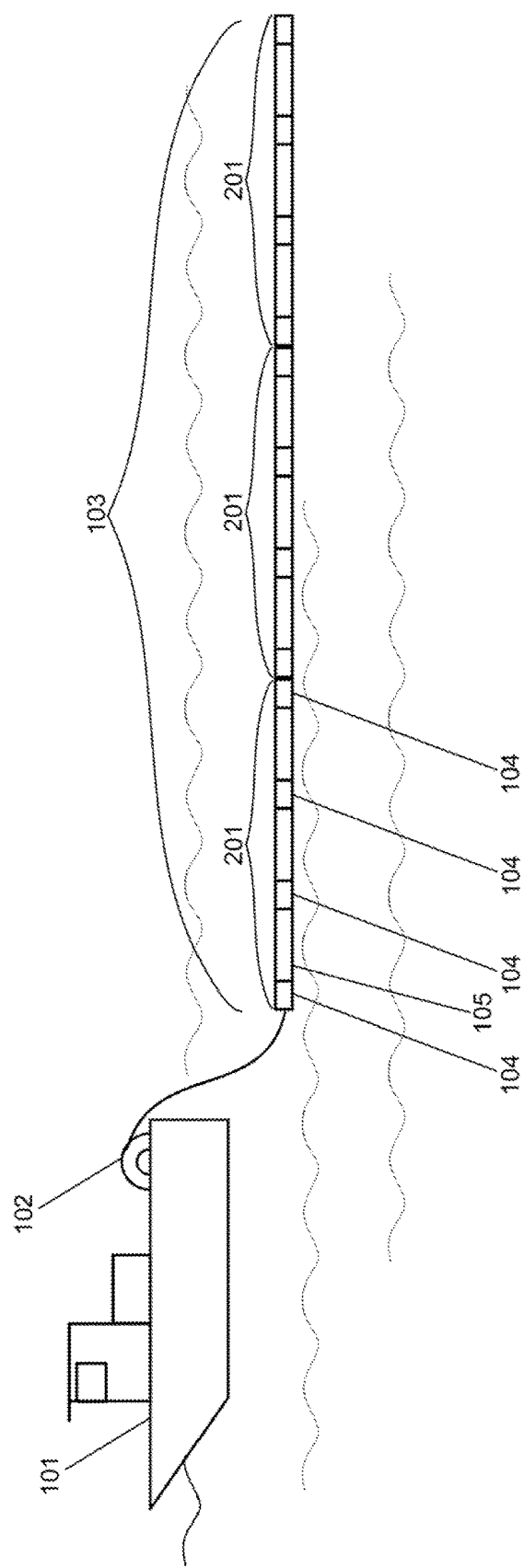
FIG. 1 depicts an exemplary marine-seismic cable system in use.
Figure 2:
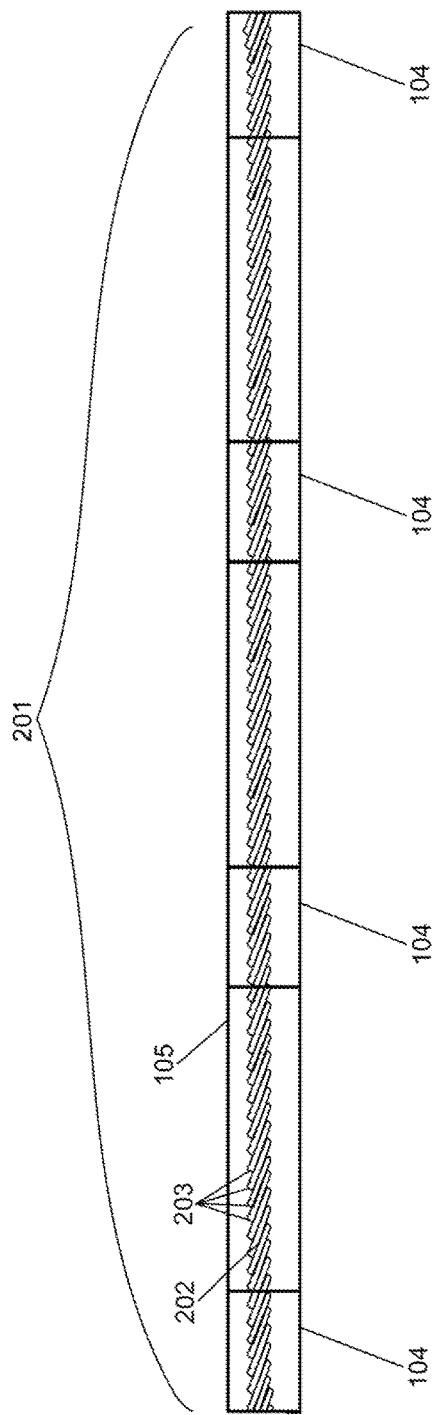
FIG. 2 depicts an exemplary section of an electro-mechanical cable including a view of a cabling layer.
Figure 3:
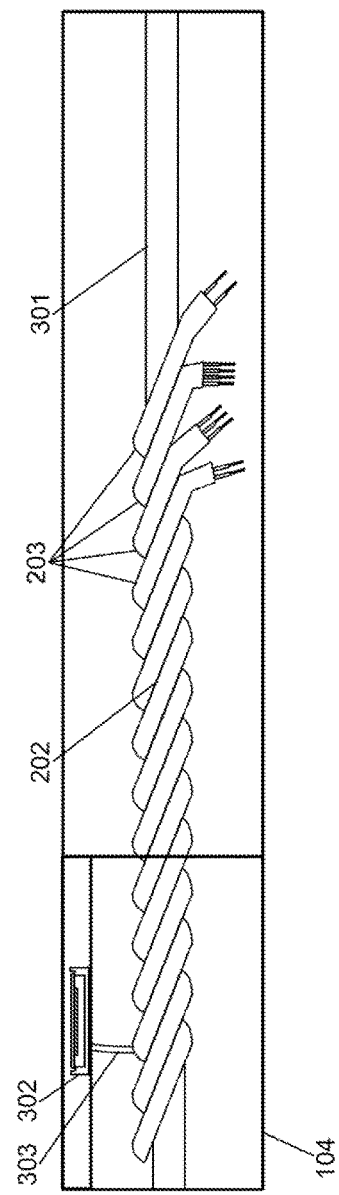
FIG. 3 depicts an exemplary portion of a section of an electro-mechanical cable including a view of internal cabling, cable conductors, and strength member.
Figure 4:
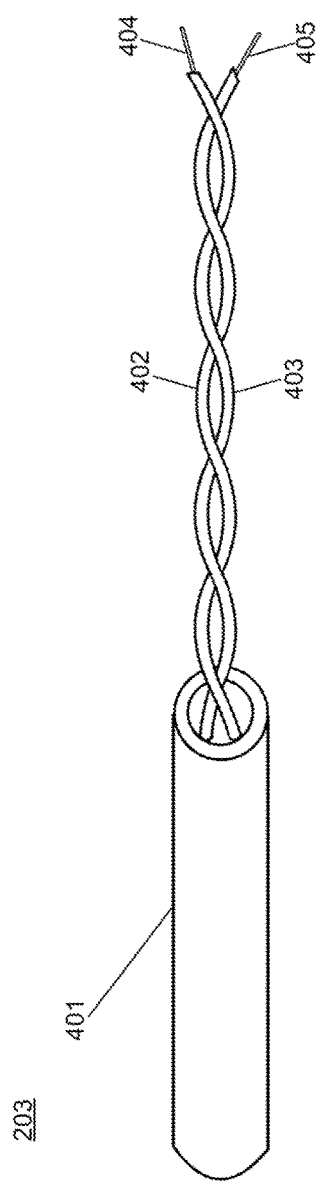
FIG. 4 depicts an exemplary twisted pair cable.

FIG. 7 depicts an exemplary portion of a section of an electro-mechanical cable including a view of the cabling layer with an overstress indicator cable, cable conductors, and strength member. Conductors in the cables 203, such as, for example, the twisted conductors 404 and 405, may be soft copper conductors. The allowable strain on copper conductors to avoid fatigue breaks may be less than 0.02%. The strain in the conductors may be reduced by twisting individual conductors, such as the conductors 404 and 405, together to form helical sub-components, such as the previously described twisted pairs, twisted triples, and twisted quads. The conductors twisted together may be kept from physically contracting by their insulation, for example, the insulations jackets 402 and 403, as depicted in FIG. 4. The helical sub-components, for example, the cables 203, may then be cabled together or wrapped around the strength member 301, as in the cabling layer 202. Every twisting operation performed on the conductors may increase the allowable elongation of and reduce the strain in the conductors allowing the cables 203 to avoid broken conductors even when subject to tensions that may be higher than the designed allowable working load for the electro-mechanical cable 103. Increasing the helix angle, the angle between windings of the cables 203 and the lengthwise axis of the strength member 301, may also increase the ability of the conductors in the cables 203 to resist breaking. The strength member 301 may be designed to withstand the anticipated mechanical loading of the electro-mechanical cable 103 and limit the strain or mechanical elongation of the electrical conductors or fiber optics.

When the electro-mechanical cable 103 is subjected to a tension higher than the designed allowable working load, the non-twisted conductors 603 and 605 in the overstress indicator cable 501 may experience greater strain than, and may break before, conductors that may be critical to the operation of the electro-mechanical cable 103, such as the conductors in the cables 203. A broken conductor 603 or 605 may be an indicator that the section 201 in which the break occurred has been overstressed during use beyond the manufacturer's recommendation. Similarly, if the overstress indicator cable 501 includes only one non-twisted conductor 603, a break in the single non-twisted conductor 603 may be an indicator that the section 201 in which the break occurred has been overstressed during use beyond the manufacturer's recommendation. The characteristics of the non-twisted conductors 603 and 605, such as material, gauge, and whether the conductors 603 and 605 are solid or stranded, may be chosen so that the conductors 603 and 605 will break when subjected to strain that is just in excess of the designed allowable working load of the electro-mechanical cable 103.

Figure 8:
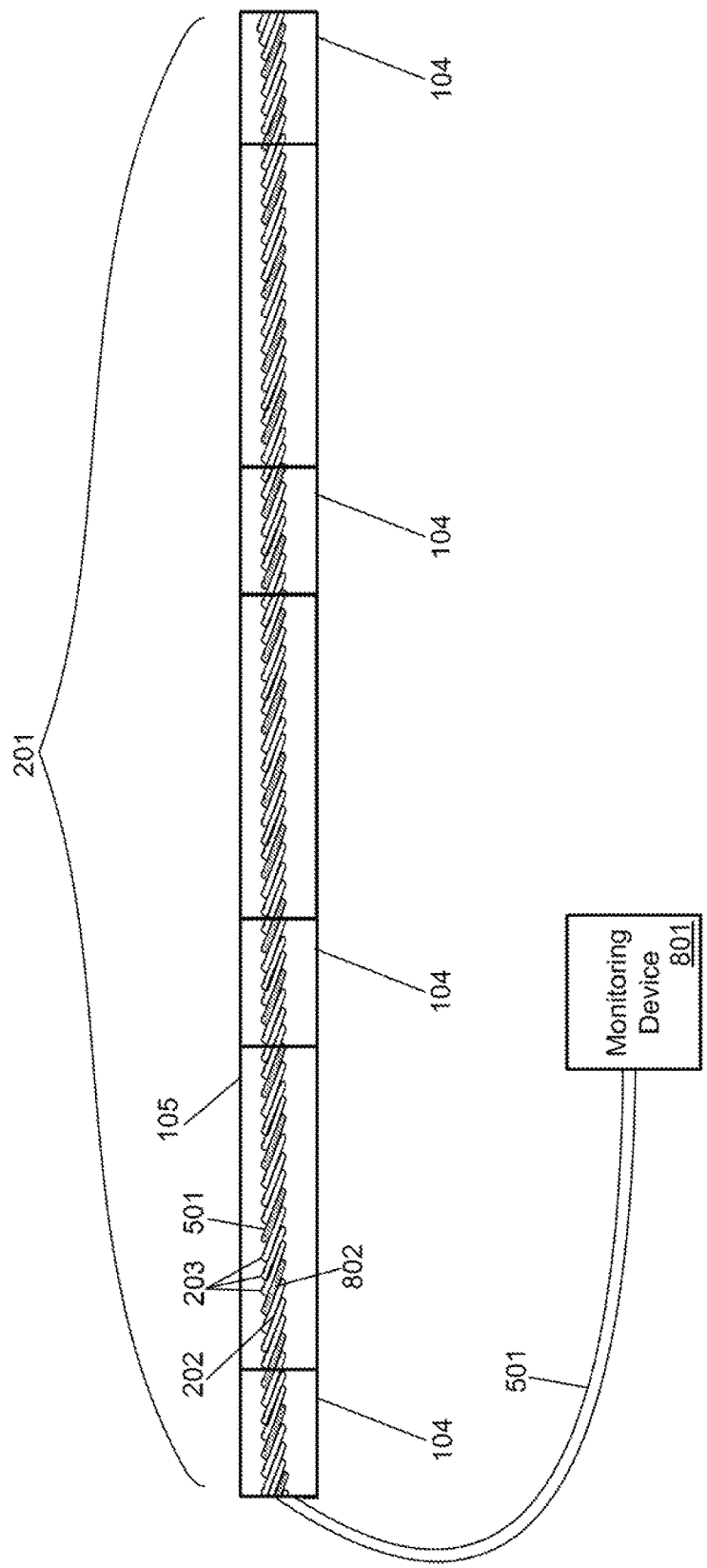
FIG. 8 depicts an exemplary section of an electro-mechanical cable connected to a monitoring device and including a view of a cabling layer with a break in an overstress indicator cable.
Figure 9:
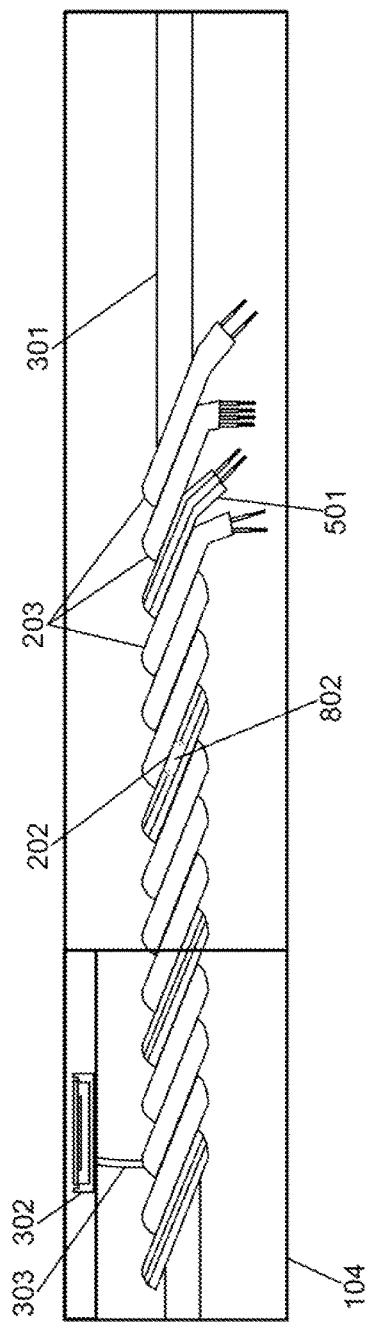
FIG. 9 depicts an exemplary portion of a section of an electro-mechanical cable including a view of the cabling layer with cable conductors, strength member, and a break in an overstress indicator cable.

FIG. 8 depicts an exemplary section of an electro-mechanical cable connected to a monitoring device and including a view of a cabling layer with a break in an overstress indicator cable. FIG. 9 depicts an exemplary portion of a section of an electro-mechanical cable including a view of the cabling layer with cable conductors, strength member, and a break in an overstress indicator cable. The overstress indicator cable 501 may be connected to a monitoring device 801. The monitoring device 801 may be located, for example, aboard the marine vessel 101, with other equipment deployed into the water by the marine vessel 101, such as, for example, a head float, or inside the corresponding section 201 where data from the monitoring device 801 may be transmitted to the marine vessel 101 along with the collected seismic data from sensor components 104. The monitoring device 801 may be any suitable device for determining when a break, for example, the break 802 depicted in FIG. 8 and FIG. 9, has occurred in one of the non-twisted conductors 603 and 605 of the overstress indicator cable 501, and may include any suitable combination of electric and electronic hardware, and software, for allowing the monitoring device 801 to monitor the overstress indicator cable 501. For example, the monitoring device 801 may be only electrical or electronic hardware with no software, or may be specialized software, or part of a larger software application, running any general or special purpose computing device capable of interfacing with the overstress indicator cable 501, either natively or through a separate hardware interface. The monitoring device 801 may be able to apply a voltage to and drive a current through the circuit created by the non-twisted conductors 603 and 605. The monitoring device 801 may include an ammeter or ohmmeter for measuring resistance and current in a circuit, and may have a visual display, such as indicator lights, an LED readout or LCD screen, auditory signaling device, such as a speaker, or may be capable of transmitting data to another device, for example using an Ethernet connection, Wi-Fi, Bluetooth, RF, or any other manner of wired or wireless data transmission.

The monitoring device 801 may function by, for example, supplying electricity to the overstress indicator cable 501. A break in the non-twisted conductor 603 may break a circuit created by the monitoring device 801 and the overstress indicator cable 501. The monitoring device 801 may detect that the circuit has been broken, which may indicate that a break has occurred in one or more of the non-twisted conductors 603 and 605. Because the current and voltage supplied by the monitoring device 801 to the overstress indicator cable 501 may only be needed to form a circuit through the non-twisted conductors 603 and/or 605, the amount of current and voltage needed to allow the monitoring device 801 to monitor the overstress indicator cable 501 may be lower than that needed to operate a series of load cells or strain gauges.

Use of the monitoring device 801 with the overstress indicator cable 501 may allow for the detection of overstress conditions in the electro-mechanical cable 103 before any of the conductors in the cables 203 break. The electro-mechanical cable 103 may then be retrieved, or the excess tension alleviated, before the operation of the electro-mechanical cable 103 is impaired.

Figure 10:
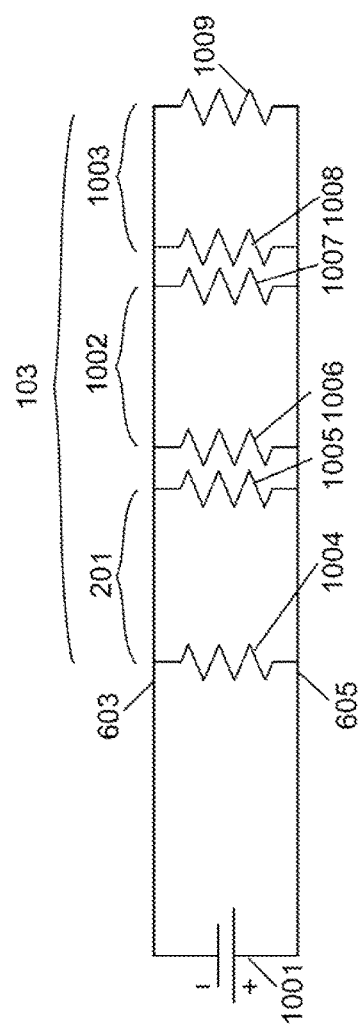
FIG. 10 depicts an exemplary circuit diagram for an overstress indicator in an electro-mechanical cable.

Each section 201 of the electro-mechanical cable 103 may have a separate overstress indicator cable 501. When a break in one of the overstress indicator cables 501 occurs, the monitoring device 801 may be able to indicate the specific section 201 of the electro-mechanical cable 103 where the break is located if, for example, the overstress indicator cables 501 are used to create a parallel circuit. FIG. 10 depicts an exemplary circuit diagram for an overstress indicator in an electro-mechanical cable. The electro-mechanical cable 103 may include the section 201, a section 1002, and a section 1003. The non-twisted conductors 603 and 605 may be connected using resistors 1004, 1005, 1006, 1007, 1008, and 1009 which may be located in suitable connectors at the beginning and end of each of the sections 201, 1002 and 1003. The connectors may also be used to connect the non-twisted conductors 603 and 605 between sections, resulting in the connectors, and resistors 1004, 1005, 1006, 1007, 1008, and 1009, being in parallel with each other across the length of the electro-mechanical cable 103. The monitoring device 801 may supply electricity to the circuit from a power source 1001, and may measure resistance or current in the circuit with, for example, an ammeter or ohmmeter which are part of or connected to the monitoring device 801. If a break occurs, the existence of the break in one of the non-twisted conductors 603 and 605 may be identified by an increase in resistance and decrease in current in the parallel circuit. The magnitude of the change in resistance and current may be used to determine the section 201 where the break occurred. The closer the break is to monitoring device 801, the greater the increase in resistance and drop in current that may be observed by the monitoring device 801. For example, if the non-twisted conductor 603 in the section 1002 breaks, the resistors 1006, 1007, 1008, and 1009 may be cut off from the parallel circuit. If the resistances of the non-twisted conductors 603 and 605 and the resistors in the connectors are known, the increase in resistance or drop in current in the circuit can be used to calculate exactly how many resistors were cut off from the circuit by the break in one of the non-twisted conductors 603 and 605. The section in which the break occurred may be determined based on the number of resistors cut off.

Other electrical schemes may be used for determining if there is a break in the overstress indicator cable 501. For example, an electrical scheme may use a single non-twisted conductor 603 or 605 to determine if there is a break. As another example, the monitoring device 801 may be placed in the section 201, and may only detect breaks in the overstress indicator cable 501 within the section 201. The monitoring device 801 may transmit this information to the marine vessel 101, as the section 201 may have processing capabilities for adding together signals from multiple sensors, digitizing them and transmitting them to the marine vessel 101. The monitoring device 801 may also locally store information on breaks detected in the overstress indicator cable 501. Each of the sections 201 may have its own monitoring device 801.

Figure 11:
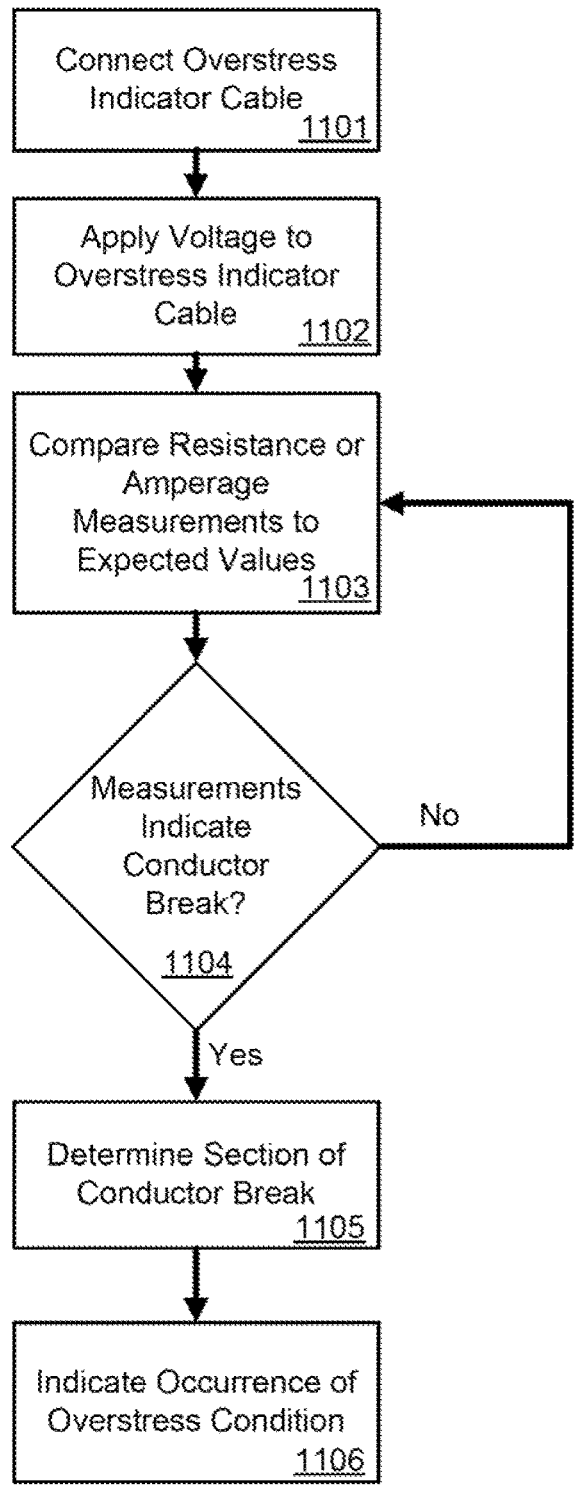
FIG. 11 depicts an exemplary procedure for detecting and indicating an overstress condition in an electro-mechanical cable with an overstress indicator cable and monitoring device.

FIG. 11 depicts an exemplary procedure for detecting and indicating an overstress condition in an electro-mechanical cable with an overstress indicator cable and monitoring device. In block 1101, an overstress indicator cable may be connected to a monitoring device. For example, one or both of the non-twisted conductors 603 and 605 in the overstress indicator cable 501 may be connected to the monitoring device 801 using any suitable connectors. If only one conductor is used, the role of the other conductor may be taken by one of cables 203, the strength member or any other available cable.

In block 1102, the monitoring device may apply a voltage to the overstress indicator cable. For example, the monitoring device 801 may use the power source 1001 to apply a voltage and drive a current through the circuit created across the electro-mechanical cable 103 by the non-twisted conductor 603 and 605 in the overstress indicator cable 501. The circuit may be, for example, the circuit depicted in FIG. 9. The current may be driven through the circuit with a known voltage.

In block 1103, the monitoring device may compare measurements from an ammeter or an ohmmeter to expected current and resistance values for the circuit. The monitoring device 801 may take resistance and amperage measurements from the non-twisted conductors 603 and 605, and compare these measurements to values that would be expected if there were no breaks in the non-twisted conductors 603 and 605. The expected values may be determined empirically, or may be calculated based on the composition of the circuit, including the number of sections 201 in the electro-mechanical cable 103, length of the overstress indicator cable 501, and the number and ratings of resistors used in the circuit.

In block 1104, if the measurements from the ammeter or ohmmeter give a resistance that is higher or amperage that is lower than expected values by an amount that is greater than expected measurement fluctuations, indicating a break in the non-twisted conductors, flow proceeds to block 1105. Otherwise, flow proceeds back to block 1103.

In block 1105, the monitoring device may determine which section the break has occurred in. Resistance that is higher than expected or amperage that is lower than expected may indicate that one of the sections 201 of the electro-mechanical cable 103 has experienced an overstress condition that broke one of the non-twisted conductors 603 and 605 in the overstress indicator cable 501. The monitoring device 801 may use the change in resistance or amperage to calculate how many resistors have been cut off from the circuit. The section 201 in which the break has occurred may then be determined based on the number of sections 201 in the electro-mechanical cable 103, number of resistors per section 201, and number of resistors cut off from the circuit. For example, if there are ten sections 201, each section 201 has two resistors, and five resistors have been cut off from the circuit, the monitoring device 801 may determine that the break in one of the non-twisted conductors 603 and 605 occurred in the eighth section 201 of the electro-mechanical cable 103.

In block 1106, the monitoring device may indicate that an overstress condition has occurred. The monitoring device 801 may indicate the existence of a break in one of the non-twisted conductors 603 and 605, signifying an overstress condition, and the section 201 in which the break has occurred, in any suitable manner. The monitoring device 801 may provide any available information, such as, for example, the time and date the break was detected, the section 201 in which the break was detected, and the ammeter or ohmmeter readings used in determining the existence of a break.

In another embodiment, it is possible to determine whether the cable had been overstressed during the repair process or after the fact of some instance. Typically, in the repair process, the continuity of the overstress indicator wire is measured and if broken, it is possible to locate the break by dissecting the cable. The dissection at the location of the break would allow the operator to determine not only if the cable had been overstressed but also if it had been stressed to the point of causing structural damage along with simple wire breaks.

The disclosed exemplary embodiments provide an apparatus for indicating overstress in an electro-mechanical cable. It should be understood that this description is not intended to limit the invention. On the contrary, the exemplary embodiments are intended to cover alternatives, modifications and equivalents, which are included in the spirit and scope of the invention as defined by the appended claims. Further, in the detailed description of the exemplary embodiments, numerous specific details are set forth in order to provide a comprehensive understanding of the claimed invention. However, one skilled in the art would understand that various embodiments may be practiced without such specific details.

Although the features and elements of the present exemplary embodiments are described in the embodiments in particular combinations, each feature or element can be used alone without the other features and elements of the embodiments or in various combinations with or without other features and elements disclosed herein.

This written description uses examples of the subject matter disclosed to enable any person skilled in the art to practice the same, including making and using any devices or systems and performing any incorporated methods. The patentable scope of the subject matter is defined by the claims, and may include other examples that occur to those skilled in the art. Such other examples are intended to be within the scope of the claims.

What is claimed is:

1. A marine electro-mechanical cable comprising:
   a strength member extending along a section of the electro-mechanical cable;
   conductors connecting plural piezoelectric seismic sensors, the conductors extending along the section of the electro-mechanical cable;
   an overstress indicator cable comprising a non-twisted conductor disposed within the section of the electro-mechanical cable; and
   an outer jacket enclosing the strength member, the overstress indicator cable, the conductors and the plural piezoelectric seismic sensors,
   wherein a characteristic of the non-twisted conductor is selected so that the non-twisted conductor breaks before the conductors when a tension in the non-twisted conductor is greater than an allowable working load for the electro-mechanical cable, and
   wherein the characteristic is at least one of a material and a gauge.

2. The marine electro-mechanical cable of claim 1, wherein the non-twisted conductor is copper.

3. The marine electro-mechanical cable of claim 1, wherein the non-twisted conductor is further adapted to break when the tension in the non-twisted conductor creates a strain in the non-twisted conductor of greater than 0.02%.

4. The marine electro-mechanical cable of claim 1, wherein the non-twisted conductor is further adapted to break when the tension in the non-twisted conductor is both greater than the allowable working load of the electro-mechanical cable and less than the tension required to break twisted pair conductors disposed in the electro-mechanical cable.

5. The marine electro-mechanical cable of claim 1, wherein the overstress indicator cable is wrapped helically around the strength member disposed lengthwise in the section of electro-mechanical cable.

6. The marine electro-mechanical cable of claim 1, wherein the overstress indicator cable is disposed in a cabling layer comprising at least one additional cable.

7. The marine electro-mechanical cable of claim 6, wherein the cabling layer is disposed within the strength member.

8. The marine electro-mechanical cable of claim 6, wherein the at least one additional cable is one of a twisted pair, twisted triple, twisted quad, and fiber optic cable.

9. The marine electro-mechanical cable of claim 1, wherein the strength member is disposed substantially in a middle of the outer jacket, the overstress indicator cable and the conductors being wrapped around the strength member.

10. The marine electro-mechanical cable of claim 1, wherein the overstress indicator cable comprises a second non-twisted conductor.

11. The marine electro-mechanical cable of claim 1, further comprising a monitoring device connected to the overstress indicator cable, wherein the monitoring device is adapted to determine if the non-twisted conductor has broken.

12. The marine electro-mechanical cable of claim 10, wherein the monitoring device is adapted to apply a voltage to the non-twisted conductors.

13. The marine electro-mechanical cable of claim 12, further comprising:
    a first connector comprising a resistor and disposed at the beginning of a first section of the electro-mechanical cable;
    a second connector comprising a resistor and disposed at the end of the first section of the electromechanical cable;
    a third connector comprising a resistor and disposed at the beginning of a second section of the electro-mechanical cable; and
    a fourth connector comprising a resistor and disposed at the end of the second section of the electro-mechanical cable,
    wherein the non-twisted conductors of the overstress indicator cable are connected to the first connector and the second connector, the second connector is connected to the third connector, and non-twisted conductors of a second overstress indicator cable disposed in the second section are connected to the third connector and the fourth connector such that the resistors of the first, second, third, and fourth connectors are in a parallel circuit.

14. A method for detecting an overstress condition in an electro-mechanical cable comprising:
    applying a voltage to a non-twisted conductor in an overstress indicator cable;
    measuring at least one characteristic of a circuit formed by the non-twisted conductor and one of a second non-twisted conductor, a strength member, and a twisted conductor;

comparing the measured characteristic to an expected value for the characteristic; and if the measured characteristic varies from the expected value for the characteristic by more than a predetermined amount, indicating that an overstress condition has occurred in the electro-mechanical cable, wherein the non-twisted conductor breaks when a tension in the non-twisted conductor is greater than an allowable working load for the electro-mechanical cable.

15. The method of claim 14, wherein the characteristic is one of amperage and resistance.

16. The method of claim 15, wherein comparing the measured characteristic to the expected value for the characteristic further comprises:

determining if a measured amperage is lower than an expected amperage.

17. The method of claim 15, wherein comparing the measured characteristic to the expected value for the characteristic further comprises:

determining if a measured resistance is greater than an expected resistance.

18. The method of claim 14, further comprising determining a section of the electro-mechanical cable in which the indicated overstress condition has occurred using the measured characteristic, the expected value for the characteristic, a physical property of the circuit, and the number of sections in the electro-mechanical cable.

19. The method of claim 18, wherein the physical property of the circuit is a quantity of resistors in the circuit in each section of the electro-mechanical cable.

20. A marine electro-mechanical cable comprising:

an outer jacket;

a strength member disposed lengthwise substantially in a middle of the outer jacket;

foam disposed inside the outer jacket;

a seismic sensor component disposed inside the outer jacket;

an overstress indicator cable, comprising non-twisted conductors, wrapped helically around the strength member within a cabling layer that also includes at least one conductor connected to the seismic sensor component, each of the non-twisted conductors comprising copper wire disposed within a respective insulation jacket, wherein the non-twisted conductors break when a tension in the non-twisted conductors is greater than an allowable working load of the electro-mechanical cable before the at least one conductor breaks;

a first connector and a second connector disposed within the electro-mechanical cable, wherein first ends of the non-twisted conductors are connected to the first connector and second ends of the non-twisted conductors are connected to the second connector; and a monitoring device comprising at least one of an ammeter and an ohmmeter connected to the overstress indicator cable, wherein the monitoring device is adapted to apply a voltage to the non-twisted conductors, measure a characteristic of a circuit formed by the non-twisted conductors, compare the measured characteristic to an expected value thereof, and, if the measured characteristic varies from the expected value by more than a predetermined amount, indicate that an overstress condition has occurred in the electro-mechanical cable the tension in the non-twisted conductors having exceeded the allowable working load of the electro-mechanical cable.

* * * * *